United States Patent [19]

Gac et al.

[11] 4,209,646

[45] Jun. 24, 1980

[54] PROCESS FOR CRYSTALLIZING AN ADDUCT OF 2,2-DI(4-HYDROXYPHENYL) PROPANE AND PHENOL

[75] Inventors: Robert Gac, Caluire; Jean-Pierre Dal Pont, Pont de Claix; Frederic Levet, Caluire, all of France

[73] Assignee: Rhone-Poulenc Industries, Paris, France

[21] Appl. No.: 836,768

[22] Filed: Sep. 26, 1977

Related U.S. Application Data

[63] Continuation of Ser. No. 627,696, Oct. 31, 1975, abandoned.

[30] Foreign Application Priority Data

Oct. 31, 1974 [FR] France .................................. 74 40170

[51] Int. Cl.² ........................ C07C 37/22; C07C 39/16
[52] U.S. Cl. .................................... 568/724; 568/718; 568/721; 260/347.8
[58] Field of Search ........... 260/621 R, 619 R, 619 A; 568/749, 724

[56] References Cited

U.S. PATENT DOCUMENTS

| | | | |
|---|---|---|---|
| 3,192,270 | 6/1965 | Meyer et al. ..................... | 260/619 R |
| 3,275,708 | 9/1966 | Bylsma ........................... | 260/619 A |

*Primary Examiner*—Werren B. Lone
*Attorney, Agent, or Firm*—Burns, Doane, Swecker & Mathis

[57] ABSTRACT

2,2-di(4-hydroxyphenyl) propane, i.e., diphenylolpropane, is purified by preparing a liquid mixture of raw diphenylolpropane, phenol and water and applying reduced pressure thereto corresponding to the vapor pressure of the mixture while simultaneously cooling same whereby an adduct of pure diphenylolpropane and phenol is crystallized.

21 Claims, 1 Drawing Figure

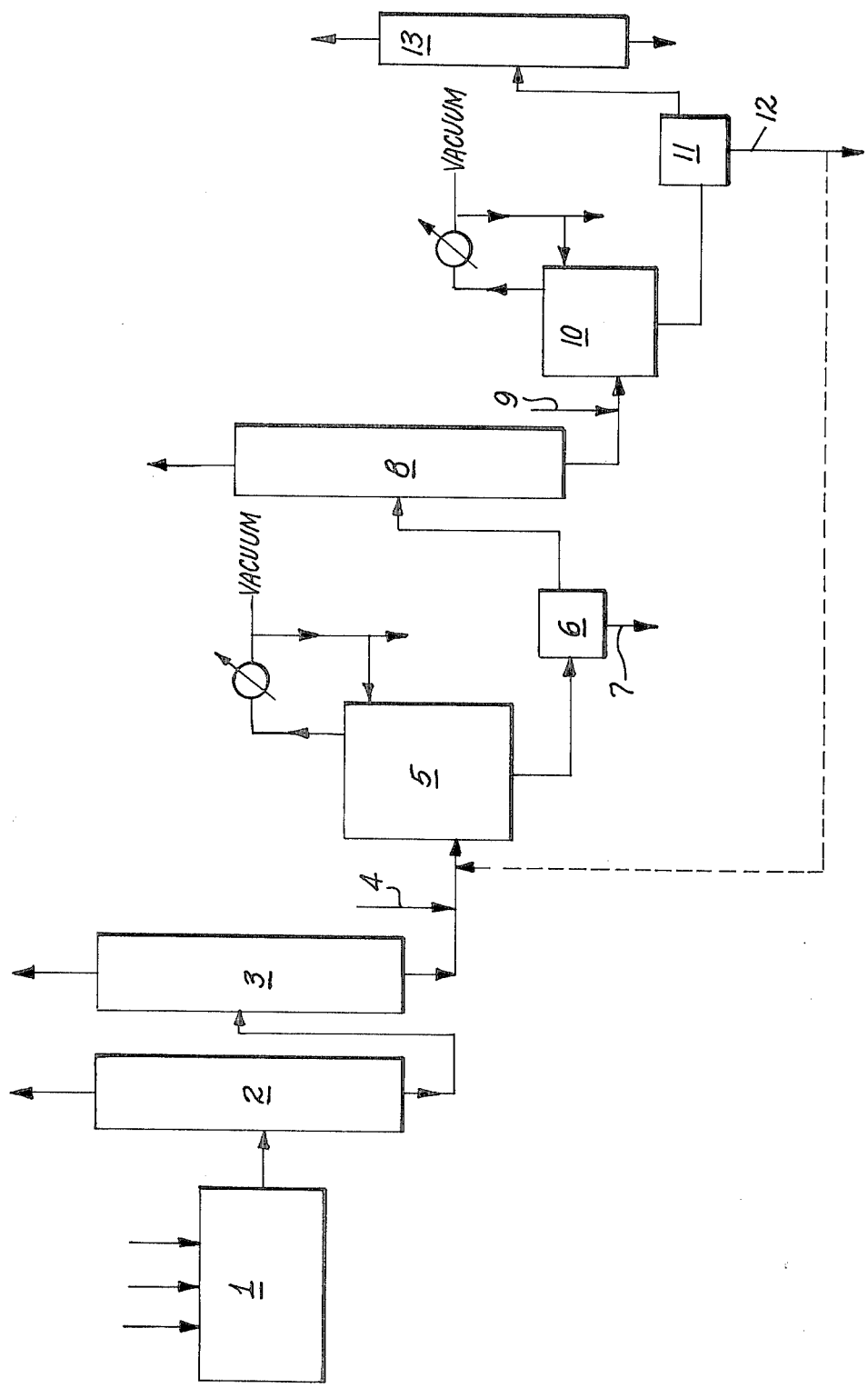

PROCESS FOR CRYSTALLIZING AN ADDUCT OF 2,2-DI(4-HYDROXYPHENYL) PROPANE AND PHENOL

CROSS REFERENCE TO RELATED DISCLOSURE DOCUMENT

This is a continuation of application Ser. No. 627,696, filed Oct. 31, 1975 now abandoned.

The present application relates to disclosure document No. 029919 deposited on Apr. 5, 1974 which is expressly incorporated herein by reference.

BACKGROUND OF THE INVENTION

The present invention relates to a process for crystallizing an adduct of 2,2-di(4-hydroxyphenyl) propane and phenol in aqueous phenol, under vacuum.

It is known that in order to obtain 2,2-di(4-hydroxyphenyl) propane (hereinafter referred to as diphenylolpropane or DPP) having a suitable purity for certain applications such as the preparation of polycarbonate resins, it is first necessary to purify the raw product. One such prior art method consists of crystallizing diphenylolpropane in a suitable solvent such as aqueous phenol. Thus, in U.S. Pat. No. 3,192,270, a process for the manufacture of pure di(hydroxyphenyl) alkanes is described which comprises dissolving these compounds in hot aqueous phenol and cooling the solution thereby precipitating crystals of the adduct of di(4-hydroxyphenyl) alkane and phenol and liberating the phenol from the adduct.

From a practical standpoint, the aforementioned process comprises the following steps: melting of the mixture resulting from the condensation of phenol and a ketone under the action of an acid catalyst, which contains the impure phenol-diphenylolalkane adduct as well as phenol; neutralizing the mixture with a concentrated aqueous solution of an alkali; separating the resulting aqueous phase; adding sufficient water to the remaining organic phase to saturate all of the phenol contained therein; decanting the mixture into two phases; separating the aqueous phase; cooling the organic phase to room temperature to allow the purified adduct of diphenylolalkane-phenol to crystallize and, lastly, separating this adduct from the mother-liquor. This process typifies prior art processes for the crystallization and purification of diphenylolpropane and it is apparent that this prior art process is overly complicated and requires excessive amounts of water.

Therefore, there exists a need for a more efficient and economical process for crystallizing diphenylolpropane.

SUMMARY OF THE INVENTION

Accordingly, it is a primary object of the present invention to provide a process for crystallizing an adduct of 2,2-di(4-hydroxyphenyl) propane and phenol to prepare pure 2,2-di(4-hydroxyphenyl) propane which obviates the problems and disadvantages inherent in prior art processes.

It is a further object of the invention to provide a process for purifying diphenylolpropane by the crystallization of a pure adduct of diphenylolpropane and phenol and to afford diphenylolpropane in a highly purified form and in good yield.

These and other objects are accomplished according to the crystallization process of the present invention wherein a mixture containing impure diphenylolpropane, phenol and a minor amount of water is prepared at a temperature at which the mixture is substantially entirely liquid, applying reduced pressure to the mixture corresponding to the vapor pressure thereof and simultaneously cooling the mixture to effectuate the crystallization of a pure adduct of diphenylolpropane and phenol.

Other objects, features and advantages of the present invention will become apparent to those skilled in the art from the accompanying FIGURE of drawing and the detailed description of the invention which follows.

BRIEF DESCRIPTION OF THE DRAWING

The FIGURE of drawing is a flow sheet diagrammatically representing the process of the present invention and the apparatus utilized therein to crystallize a pure adduct of diphenylolpropane and phenol and recover purified diphenylolpropane.

DETAILED DESCRIPTION OF THE INVENTION

According to the process of the present invention, a mixture containing impure diphenylolpropane, phenol and less than about 15% by weight of water is prepared at a temperature at which the mixture is entirely liquid and then cooled to a temperature less than about 60° C. while applying reduced pressure to the mixture which pressure approximately corresponds to the vapor pressure of the reaction mixture whereby an adduct of pure diphenylolpropane and phenol is crystallized.

Applicants have surprisingly discovered that if crystallization of the diphenylolpropane-phenol adduct is effectuated under vacuum that the amount of water in the starting mixture necessary for the crystallization process can be significantly reduced, e.g., to as little as 2% or less by weight with respect to the mixture, and further that the solubility of the adduct in the crystallization medium is enhanced which favors crystallization yield.

The liquid mixture to be crystallized typically contains raw diphenylolpropane to be purified, phenol and water. Raw diphenylolpropane as utilized herein means the product resulting from the manufacture thereof which is generally constituted principally with 2,2-di(4-hydroxyphenyl) propane and with various impurities, particularly isomers of diphenylolpropane and compounds such as 2,2,4-trimethyl(4-hydroxyphenyl) chromane (also referred to as co-dimer) and the like. The raw diphenylolpropane which is supplied to the starting mixture of the invention may be obtained by any conventional method such as, for example, by the condensation of phenol and acetone in the presence of an acid catalyst such as hydrochloric acid. The amount of raw diphenylolpropane present in the liquid mixture is not in the least critical and may vary over a wide range up to the point of saturation which generally should not be exceeded. An amount of raw diphenylolpropane ranging between 10% and 55% based upon the total weight in the mixture has been found to be generally suitable. The amount of water present in the initial mixture is, however, somewhat critical and should be comprised between about 2 and 12% by weight and, preferably, 4 to 8%. When the mixture is introduced into the crystallization zone, the temperature of the mixture is generally that at which all of the components in the mixture are substantially in the liquid state. A temperature of between about 70° and 100° C. has been found to be particularly satisfactory for maintaining the components in a liquid state.

The starting mixture may be prepared by heating suitable amounts of phenol, water and raw diphenylolpropane to a predetermined temperature. According to a preferred embodiment of the present invention, when the manufacture of diphenylolpropane is carried out in the presence of a large excess of phenol which is generally consistent with most commercial processes, the mixture to be crystallized is directly prepared from the reaction medium utilized in the manufacture of diphenylolpropane without preliminary separatory steps except for the removal of the catalyst utilized in the reaction. Optionally, the reaction mixture to be crystallized is first concentrated by distillation of a portion of the phenol and a suitable amount of water is added to the liquid remaining.

During the crystallization process of the present invention, the starting mixture described hereinabove is cooled to a temperature between about 25° and 60° C., preferably 40° to 50° C., under reduced pressure essentially corresponding to the vapor pressure of the crystallization medium. The vapor phase is primarily comprised of water, but also contains a small amount of phenol. The vapor pressure observed varies with the relative ratio of water in the initial mixture and the cooling temperature selected. Generally, with the temperatures and water ratios utilized herein, the vapor pressure will be between about 20 and 120 mmHg. As stated previously, the reduced pressure applied to the crystallization zone generally corresponds to the vapor pressure of the mixture and in view of the relatively low vapor pressures prevailing under the condition in the crystallization zone, the vacuum applied to the system is likewise minimal so that the process of the invention is easily carried out.

Some examples of vapor pressures are indicated in Table 1 below for various initial mixtures and crystallization temperatures according to the present invention.

TABLE 1

| Initial Mixture | | Vapor pressure (mm Hg) for various crystallization temperatures | | | |
| --- | --- | --- | --- | --- | --- |
| Precentage of diphenylol propane (% by weight) | Water ratio (% by weight) | 40° C. | 45° C. | 50° C. | 60° C. |
| 10 | 5 | 33.5 | | | |
| 10 | 5 | | | | ~77 |
| 10 | 8 | ~38 | | | |
| 10 | 8 | | | | ~89 |
| 10 | 11 | 45.5 | | | |
| 10 | 11 | | | | ~112 |
| 25 | 6 | ~35 | | | |
| 30 | 6.5 | | ~42 | | |
| 38 | 9 | | | ~58 | |
| 50 | 4 | | | 35 | |
| 50 | 5 | | | 40 | |

From the foregoing table, it is apparent that the vapor pressure varies independently of the diphenylolpropane concentration in the initial mixture and depends on the amount of water in the mixture as well as the crystallization temperature.

According to a preferred embodiment of the present invention, the vapor phase may be extracted from the crystallization zone and all or part thereof advantageously condensed and returned to the crystallization zone either continuously or discontinuously.

The crystals obtained from the crystallization zone consist of a pure adduct of diphenylolpropane and phenol containing approximately equimolar amounts of the respective components. The crystals are separated from the mother-liquor, utilizing conventional separatory techniques including washing and subsequently treated to eliminate the phenol component. Phenol may be removed from the adduct by any of the methods heretofore employed, such as extraction, distillation or steam stripping.

The mother-liquor remaining after the separation of the crystals as described above still contains a minor amount of diphenylolpropane. The residual diphenylolpropane may be utilized without modification for the preparation of a new liquid mixture to be crystallized according to the present invention. Of course, the diphenylolpropane may be distilled in order to recover aqueous phenol therefrom which can also be recycled. However, according to a particularly advantageous embodiment of the present invention, the mother-liquor may be crystallized to obtain an even higher crystallization yield. For example, the mother-liquor may be concentrated up to a desired diphenylolpropane ratio by distilling a part of the phenol off and adjusting the water ratio so that a mixture is obtained which may be reheated to a substantially liquid form and then crystallized according to the process of the present invention.

Diphenylolpropane which is crystallized from the mother-liquor as described immediately above may be used directly, after elimination of phenol, for various applications. However, if diphenylolpropane of the same high degree of purity as that obtained according to the crystallization process herein is desired, the adduct of diphenylolpropane-phenol or only diphenylolpropane collected from the mother-liquors is utilized in the preparation of a liquid mixture used as the feed in the instant crystallization process.

The present process can be carried out with equivalent results either discontinuously or continuously. Carrying out the present crystallization process continuously is particularly advantageous. Even after several hours, the crystallization apparatus remains unobstructed. Moreover, the present crystallization process requires no stirring or only moderate stirring thus avoiding physical degradation of the crystals formed which is a serious disadvantage of heretofore utilized crystallization systems based on cooling at ordinary pressures which require strong stirring of the mixture to eliminate the calories produced which concomitantly causes the adduct crystals being formed to break apart. The diphenylolpropane obtained from the pure crystallized adduct is of such purity and whiteness that it can be directly employed in applications wherein high purity of the diphenylolpropane starting material is essential, such as in the manufacture of polycarbonate resins. The crystallization yield is very high and generally exceeds 90%.

The crystallization process of the present invention may be typically integrated in a process for the manufacture of diphenylolpropane. The overall integrated process will generally include the following steps described with reference to the accompanying schematic diagram of FIG. 1.

In zone 1, acetone is reacted with a large excess of phenol, for example, 6 to 10 moles of phenol for each mole of acetone in the presence of gaseous hydrochloric acid and a predetermined amount of water, such as 3 to 10% by weight at a temperature from about 20° to 50° C. until all of the starting acetone has been converted.

Generally the initial reaction is carried out in several reactors.

The reaction mixture from zone 1 is next subjected to two distillations in columns 2 and 3 to first remove hydrochloric acid and water and then a sufficient amount of phenol so that the distillation bottoms contain the desired amount of raw diphenylolpropane and phenol for subsequent crystallization. The first distillation is, preferably, carried out under reduced pressure, for example, between 30 and 50 mm Hg and the distillate head from column 2 comprises an aqueous solution of hydrochloric acid containing a small amount of phenol. This solution is then treated to recover the respective constituents, for example, according to the method described in U.S. Pat. No. 3,829,509, filed Nov. 24, 1969 and incorporated herein by reference. The second distillation is likewise advantageously effected under a reduced pressure which is approximately the same as that in the first column. The distilled phenol can be recovered and recycled to any stage of the process.

The bottoms from column 3 are drawn off and an amount of water equal to about 2 to 12% by weight with respect to the total mixture is added via inlet 4 to prepare a mixture in zone 5 from which the pure diphenylolpropane-phenol adduct is crystallized according to the present invention.

The crystals are separated from the mother-liquor in zone 6 by filtration or centrifugation, for example, and drawn off at 7 and subsequently treated to eliminate phenol therefrom as described hereinabove.

In column 8, the mother-liquor from zone 6 is distilled to remove an amount of phenol sufficient to provide a distillation bottom containing the desired proportions of raw diphenylolpropane and phenol for subsequent crystallization. The distilled phenol entrains the water present in the mother-liquor and may, for example, be recycled for condensation with acetone.

The bottoms of the preceding distillation are drawn off and an amount of water comprising between about 2 to 12% by weight with respect to the total mixture is added thereto at inlet 9 and a fresh crystallization of diphenylolpropane-phenol adduct is effected from this mixture in zone 10.

Again, the crystals are separated from the mother-liquor in zone 11 and collected in zone 12 and either processed for the removal of phenol or introduced into the mixture of the initial crystallization zone.

Complete distillation of the phenol present in the mother-liquor obtained in zone 11 is carried out in column 13, preferably under reduced pressure. The phenol entrains the water present in the mother-liquor and it may be used for condensation with acetone. The final distillation bottom in column 11 is generally comprised of unusable impurities and may be discarded.

The integrated process described above including the various recycling and product recovery stages provided for therein permits the continuous obtention of diphenylolpropane of extremely high purity in a simple, efficient process which is totally acceptable from a commercial production standpoint.

The following non-limitative examples further illustrate the present invention.

EXAMPLE 1

A crystallization zone is continuously fed at a rate of 50 l./hour at approximately 85° C. with a liquid mixture comprising (by weight):
    raw diphenylolpropane: 50% (with 3% of impurities)
    water: 5%
    phenol: 45%

In the crystallizer, the temperature is maintained at about 45° C. and the vapor pressure is 40 mm Hg. and the residence time is one hour. The vapor phase extract is condensed in a heat exchanger the cooling water of which is at 20° C. and the condensate is recycled entirely to the crystallizer.

The crystallization slurry is continuously drawn off from the crystallization zone and dried in a centrifuge at 1000 g. After 60 hours, 1800 kg. of adduct crystals are collected and subsequently washed and dried. 1600 kg. of diphenylolpropane-phenol adduct are obtained containing 70% by weight of diphenylolpropane and 30% by weight of phenol. The diphenylolpropane contains less than 0.2% by weight of impurities. The crystals of adduct have a coloration corresponding to 30 A.P.H. after melting.

EXAMPLE 2

The procedures of Example 1 are repeated. The mother-liquors of crystallization are concentrated by distillation under 200 mm Hg. and 160° C. to obtain a bottom fraction comprised of phenol and 55% by weight of raw diphenylolpropane. Four percent by weight of water is added to this mixture and the mixture heated to maintain a temperature of about 90° C. The mixture is then crystallized at 50° C. under 35 mm Hg. After drying and washing, 40 parts of adduct are collected from 100 parts of the initial mixture with the adduct having 2% by weight of impurities relative to the weight of diphenylolpropane.

The above examples and disclosure are set forth merely for illustrating the mode and the manner of the invention and, while various modifications and embodiments can be made by those skilled in the art, in the light of this invention, they are made without departing from the spirit of the invention. It is intended, therefore, that the invention be limited only by the scope of the claims which follow.

What is claimed is:

1. A process for crystallizing an adduct of pure diphenylolpropane and phenol, which comprises (i) preparing a liquid mixture of impure diphenylolpropane, phenol and water, said mixture comprising less than about 15% by weight of water and said mixture being prepared at a temperature sufficient to maintain same in a substantially liquid state, but not in excess of about 100° C., (ii) cooling said substantially liquid mixture to a temperature at least as low as about 60° C., while (iii) simultaneously applying thereto a vacuum essentially corresponding to the vapor pressure of the vapor phase of said mixture, and (iv) whereby an adduct of pure diphenylolpropane and phenol is crystallized.

2. The process as defined by claim 1, wherein said liquid mixture is comprised of between about 2 to 12% by weight of water based on the weight of said mixture.

3. The process as defined by claim 2, wherein the amount of water is between about 4 to 8%.

4. The process as defined by claim 1, wherein said liquid mixture is comprised of no greater than about 2% of water.

5. The process as defined by claim 1, wherein the amount of diphenylolpropane present in said mixture ranges between about 10% and 55% based on the weight of said mixture.

6. The process as defined by claim 1, wherein said preparing is carried out at a temperature between about 70° C. and 100° C.

7. The process as defined by claim 1, wherein said cooling is effected at a temperature between about 25° C. and 60° C.

8. The process as defined by claim 7, wherein said temperature is between about 40° C. and 50° C.

9. The process as defined by claim 1, wherein said vacuum is between about 20 and 120 mm Hg.

10. The process as defined by claim 1, further comprising recovering said adduct and removing phenol therefrom.

11. The process as defined by claim 1, wherein said vapor phase is removed and condensed, and at least part thereof recycled in said process.

12. The process as defined by claim 1, wherein said process is carried out continuously.

13. The process as defined by claim 1, wherein said process is carried out discontinuously.

14. The process as defined by claim 1, wherein said diphenylolpropane to be purified comprises the reaction product obtained by the condensation of phenol and acetone in the presence of an acid catalyst.

15. The process as defined by claim 1, further comprising separating crystals of said adduct from said mixture, adjusting the water content of the remaining mother-liquor to no greater than about 12% by weight, to form a second mixture, maintaining said second mixture in a substantially liquid state and cooling same to between 25° C. and 60° C. under a reduced pressure substantially equal to the vapor pressure of said second mixture to crystallize an adduct of pure diphenylolpropane and phenol from said second mixture.

16. The process as defined by claim 15, wherein prior to adjusting the water content thereof, said mother-liquor is concentrated by distillation of a portion of the phenol present therein.

17. The process as defined by claim 1, said process being conducted under no more than moderate stirring.

18. The process as defined by claim 1, wherein said impure diphenylolpropane comprises impurities selected from the group consisting of isomers of diphenylolpropane, 2,2,4-trimethyl(4-hydroxyphenyl)chromane, and mixtures thereof.

19. A process for crystallizing an adduct of pure diphenylolpropane and phenol, which comprises (i) preparing a liquid mixture of impure diphenylolpropane, phenol and water, said mixture comprising less than about 15% by weight of water and said mixture being prepared at a temperature sufficient to maintain same in a substantially liquid state, but not in excess of about 100° C., (ii) cooling said substantially liquid mixture to a temperature at least as low as about 60° C., while (iii) simultaneously applying thereto a vacuum essentially corresponding to the vapor pressure of the vapor phase of said mixture, said vapor pressure varying independently of the diphenylolpropane concentration in the mixture (i) but dependently upon the less than 15% by weight water in said mixture and dependently upon the cooling temperature (ii) at least as low as about 60° C., and (iv) whereby an adduct of pure diphenylolpropane and phenol is crystallized.

20. A process for crystallizing an adduct of pure diphenylolpropane and phenol, which process essentially consists of (i) preparing a liquid mixture of impure diphenylolpropane, phenol and water, said mixture comprising less than about 15% by weight of water and said mixture being prepared at a temperature sufficient to maintain same in a substantially liquid state, but not in excess of about 100° C., (ii) cooling said substantially liquid mixture to a temperature at least as low as about 60° C., while (iii) simultaneously applying thereto a vacuum essentially corresponding to the vapor pressure of the vapor phase of said mixture, said vapor pressure varying independently of the diphenylolpropane concentration in the mixture (i) but dependently upon the less than 15% by weight water in said mixture and dependently upon the cooling temperature (ii) at least as low as about 60° C., and (iv) whereby an adduct of pure diphenylolpropane and phenol is crystallized.

21. A process for crystallizing an adduct of pure diphenylolpropane and phenol, which comprises (i) preparing a substantially liquid mixture of impure diphenylolpropane, phenol and water, said mixture comprising less than about 15% by weight of water and said mixture being prepared at a temperature within the range of from about 70° C. to about 100° C., (ii) cooling said substantially liquid mixture to a temperature within the range of from about 25° C. to about 60° C., while simultaneously applying thereto a vacuum essentially corresponding to the vapor pressure of the vapor phase of said mixture and said vacuum being within the range of from about 20 to 120 mm Hg., and (iv) whereby an adduct of pure diphenylolpropane and phenol is crystallized.

* * * * *